(12) United States Patent
Moulton et al.

(10) Patent No.: US 9,199,054 B2
(45) Date of Patent: Dec. 1, 2015

(54) ARTICULATING HEADGEAR CONNECTOR FOR RESPIRATORY MASKS

(71) Applicant: Sleepnet Corporation, Hampton, NH (US)

(72) Inventors: Thomas M. Moulton, Rye, NH (US); Sameer Kulkarni, Hampton, NH (US); Robert F. Moore, Jr., Salem, NH (US)

(73) Assignee: Sleepnet Corporation, Hampton, NH (US)

( * ) Notice: Subject to any disclaimer, the term of this patent is extended or adjusted under 35 U.S.C. 154(b) by 416 days.

(21) Appl. No.: 13/714,881

(22) Filed: Dec. 14, 2012

(65) Prior Publication Data
US 2013/0276790 A1 Oct. 24, 2013

Related U.S. Application Data

(60) Provisional application No. 61/636,907, filed on Apr. 23, 2012.

(51) Int. Cl.
A61M 16/00 (2006.01)
A61M 16/06 (2006.01)
A61M 16/08 (2006.01)

(52) U.S. Cl.
CPC ....... *A61M 16/0683* (2013.01); *A61M 16/0057* (2013.01); *A61M 16/06* (2013.01); *A61M 16/0816* (2013.01)

(58) Field of Classification Search
CPC ............... A61M 16/0633; A61M 16/0638; A61M 16/065; A61M 16/0683; A61M 16/0825; A62B 18/084; A62B 9/04
USPC .................................................... 128/207.11
See application file for complete search history.

(56) References Cited

U.S. PATENT DOCUMENTS 3,117,574 A * 1/1964 Replogle ............... 128/206.27
3,330,274 A * 7/1967 Bennett .................. 128/206.26

(Continued)

FOREIGN PATENT DOCUMENTS

EP 1234593 8/2002

OTHER PUBLICATIONS

Philips Healthcare, "TrueBlue—your complete package", website article from www.healthcare.philips.com, 2011, Koninklijke Philips Electronics NV, Amstelplein 2, Breitner Center, Amsterdam, 1096 BC, Netherlands.

*Primary Examiner* — Lynne Anderson
*Assistant Examiner* — Kathryn E Ditmer
(74) *Attorney, Agent, or Firm* — Donald S. Holland, Esq.; Holland & Bonzagni, P.C.

(57) ABSTRACT

Applicants have disclosed an "Articulating Headgear Connector for Respiratory Masks" which allows three-dimensional movement of the headgear connector to alleviate the mechanical forces incurred from a wearer's head movement, and thus maintain an effective seal. In the preferred embodiment, the invention comprises: a CPAP mask having a plastic shell; the mask has a stub tube extending outwardly from the shell; a headgear connector mounted loosely onto the stub tube; a T-shaped nib on the elbow guides the headgear's movement; whereby the headgear connector can slide forward on the stub tube (i.e., move along the Z axis), guided by the nib; and, whereby the headgear connector can rock (i.e., about the X-Y axes) and its sides seesaw on the stub tube (i.e., along the Z-axis), with the amount of rotation and seesawing limited by the nib.

2 Claims, 5 Drawing Sheets

(56) References Cited

U.S. PATENT DOCUMENTS

| | | | |
|---|---|---|---|
| 5,662,101 A * | 9/1997 | Ogden et al. | 128/205.25 |
| 5,921,239 A * | 7/1999 | McCall et al. | 128/205.25 |
| 6,631,718 B1 | 10/2003 | Lovell | |
| 7,353,827 B2 * | 4/2008 | Geist | 128/207.11 |
| 7,726,309 B2 | 6/2010 | Ho et al. | |
| 2004/0094160 A1 * | 5/2004 | McDonald | 128/207.17 |
| 2006/0005840 A1 * | 1/2006 | Cannon | 128/207.11 |
| 2006/0272646 A1 | 12/2006 | Ho et al. | |
| 2007/0044797 A1 * | 3/2007 | Ho | 128/204.18 |
| 2008/0314388 A1 * | 12/2008 | Brambilla et al. | 128/205.25 |
| 2010/0012128 A1 * | 1/2010 | Takishita et al. | 128/206.24 |
| 2011/0162654 A1 | 7/2011 | Carroll et al. | |
| 2014/0230821 A1 * | 8/2014 | Warters et al. | 128/205.25 |

* cited by examiner

ARTICULATING HEADGEAR CONNECTOR FOR RESPIRATORY MASKS

RELATED APPLICATION

This application claims priority from Applicants' U.S. Provisional Patent Application Ser. No. 61/636,907, filed Apr. 23, 2012. Applicants claim the benefit of priority from that provisional application. Applicants hereby incorporate by reference the entire disclosure of that provisional application.

FIELD OF INVENTION

This invention relates to respiratory masks in general. More particularly, it relates to a headgear connector with an articulating mechanism.

BACKGROUND OF THE INVENTION

There is a growing need for supplemental respiratory support for patients in the hospital and home environment. Positive pressure ventilation, in which a supply of pressurized air is delivered to the patient's airway, is often used. Positive pressure ventilation has been used to treat respiratory failure, respiratory insufficiency, and sleep apnea. There are a variety of patient interfaces that can be used to provide positive pressure ventilation including masks and nasal cannula. Mask interfaces are available for home and hospital use with many designs including nasal, oronasal (covering the nose and mouth), and full face masks.

Mask assemblies comprise a shell of rigid or pliable material (e.g., plastic) with a face-contacting cushion (e.g., a gel-filled bladder) that is held in place with headgear (e.g., straps). The shell provides the structure for the headgear connectors and elbow assembly. The cushion provides a seal against the patient's face creating a cavity around the airway through which positive pressure ventilation can be applied. Headgear connectors can be built into the mask or snapped onto the shell. Most headgear connectors center on the elbow assembly.

A common problem with existing mask technologies is the tendency for a broken or ineffective seal. Mechanical forces exerted on the mask when a patient changes position are often enough to break the seal. As the patient changes position, the headgear tends to slip between the patient's head and the bed, exerting a mechanical force on the mask in the opposite direction of the movement. This force tends to pull the mask, causing mask slippage. That slippage is often enough to break the seal. The noise and discomfort, from the broken seal, is usually enough to wake or stir the patient. The patient or attendant then needs to refasten the mask to obtain an effective seal.

If a mask is used for the administration of Continuous Positive Airway Pressure ("CPAP") treatment for the condition of obstructive sleep apnea, such a leak can drop the pressure, and amount of breathable air, provided to the mask wearer. Thus, treatment becomes ineffective. If the patient does not wake as a result of the leak, the patient can go potentially without treatment for a long period of time. Alternatively, if the mask is used for the treatment of respiratory insufficiency in a hospital environment, the leak will induce alarms from the ventilation device that will alert hospital staff. While there is minimal risk for the patient to be without treatment for a long period of time, the patient will still have disrupted sleep.

There have been numerous attempts, by different manufacturers, to design a mask that will maintain equal pressure on both sides of the mask when the head is rotated from side to side. The earliest attempts resulted in masks that were uncomfortable to wear, reducing the rate of patient compliance. In recent years, manufacturers have focused on comfort when designing masks that can maintain an effective seal during movement. Manufacturers have tried to combat the leak issue by increasing the size of the cushion, changing its shape, or using material (e.g., a gelatinous material inside a thin bladder) that easily conforms to the patient's face. An increased cushion size, for example, can increase comfort and flexibility of the mask allowing it to maintain an effective seal by conforming to the patient's movements. Other manufactures have tried to alter the structure of the mask shell or the materials used to make the headgear connector.

One example of a mask that relies on a larger cushion size is the ResMed Mirage™ SoftGel nasal mask as described in U.S. patent application Ser. No. 12/736,980, Publication No. 2011/0162654, filed by Carroll et al. The Mirage™ mask design includes a gel cushion with two layers. The internal layer of the gel is softer than the outer layer. The outer layer provides structure for the cushion and comprises the face contacting portion. There is a plastic frame attached to the cushion that snaps into the mask shell. The frame fits into grooves on the mask contacting portion of the gel cushion. The cushion provides flexibility, allowing the Mirage™ mask to move somewhat with the patient. Its frame, however, does not hold the cushion securely, especially when a wearer tosses and turns while sleeping. During such movement, the cushion can give way when the patient moves creating a leak between the frame and cushion. This design also contributes to excessive mask weight, which can lead to reduced patient comfort.

Another invention attempts to reduce leaks by adding flexibility within the mask structure. Respironics' TrueBlue™ nasal mask combines a few of the manufacturer's technologies. The mask design relies on an accordion shaped tube (a.k.a. "freeform spring") between the mask shell and elbow to provide flexibility within the mask structure. It has a "3-point" headgear connector anchored to the mask, with an elbow in the center. There are two points with slots to receive the headgear straps on either side of the elbow. There is one point at the top of the connector attached to a forehead pad with two slots for headgear straps. The headgear connector is rigid, but the mask shell is designed to flex easily, alleviating some tension between the headgear connector and headgear straps. The headgear attaches to talons that snap into the headgear connector, which allows the headgear to have added flexibility. While the freeform spring design may withstand mechanical forces from movement during sleep, the elongated mask shape may cause the patient to have to breathe out with more force to expel unwanted carbon dioxide. A buildup of carbon dioxide in the TrueBlue™ mask could be harmful to the patient.

Another invention attempts to reduce leaks by using a flexible headgear connector (a.k.a. "glider strap"). Fisher & Paykel's Flexfit™ 432 full face mask incorporates a wire headgear connector that snaps in to the front of the mask. The glider strap slides from side to side, providing freedom of movement while maintaining a seal. The sliding movement allows the headgear connector to withstand the mechanical forces from movement when the head is rotated side to side. One issue with the Flexfit™ 432 design is the ease with which the headgear connector can be dislodged from the mask. Once the headgear connector becomes dislodged, it is difficult to reattach.

Accordingly, it is a primary object of the present invention to a headgear connector for CPAP masks that can articulate three dimensionally (i.e., in the X-Y-Z planes) with the force incurred during a patient's movement, thus maintaining an effective seal.

It is another general object to provide a headgear connector design suitable for different types of respiratory masks.

It is another general object to provide a headgear connector, commensurate with the above-listed objects, which is safe and durable to use.

SUMMARY OF THE INVENTION

Applicants have disclosed a uniquely shaped headgear connector with an articulating mechanism that allows 3-dimensional movement to hold the mask in a sealing position while sleeping. In the preferred embodiment, the headgear connector and the mask are designed to create an articulating mechanism that allows the headgear connector to rock back and forth in the same plane as the mechanical forces. As the force pulls the mask, the headgear connector rocks in the direction of the force relieving its effect. The headgear connector is the only component that moves, while the mask remains steady on the patient's face without breaking the seal.

In the preferred embodiment, a stub tube (i.e., a stub tube attached to an inlet of the mask shell) has a generally T-shaped nib or guard rail which allows for the rotation, rocking, and locking of the headgear connector. The nib guides and limits the connector's movement in the X-, Y-, and Z-axes and thus changes the range of motion.

The headgear connector can be used on a variety of patient interfaces including nasal, oronasal, or full face masks used for positive airway pressure therapy.

DESCRIPTION OF THE DRAWINGS

The above and other objects of the current invention will become more readily understood when the following text is read in conjunction with the accompanying drawings, in which.

DETAILED DESCRIPTION OF THE PREFERRED EMBODIMENTS

As shown in FIGS. 1-9, Applicants have disclosed an "Articulating Headgear Connector for Respiratory Masks" which allows three-dimensional movement of the headgear connector to alleviate the mechanical forces incurred from a wearer's head movement, and thus maintain an effective seal. FIGS. 1-6 disclose a preferred embodiment of Applicants' invention, while FIGS. 7-9 disclose three alternate embodiments.

The depicted mask(s) and its components (e.g., headgear connector, gel cushion) are manufactured in the manner described in U.S. Pat. No. 6,631,718 to John R. Lovell, with additions described herein. Sleepnet Corporation is the Assignee of both U.S. Pat. No. 6,631,718 and the present application. Applicants hereby incorporate by reference the entire disclosure of U.S. Pat. No. 6,631,718.

Figure 1:
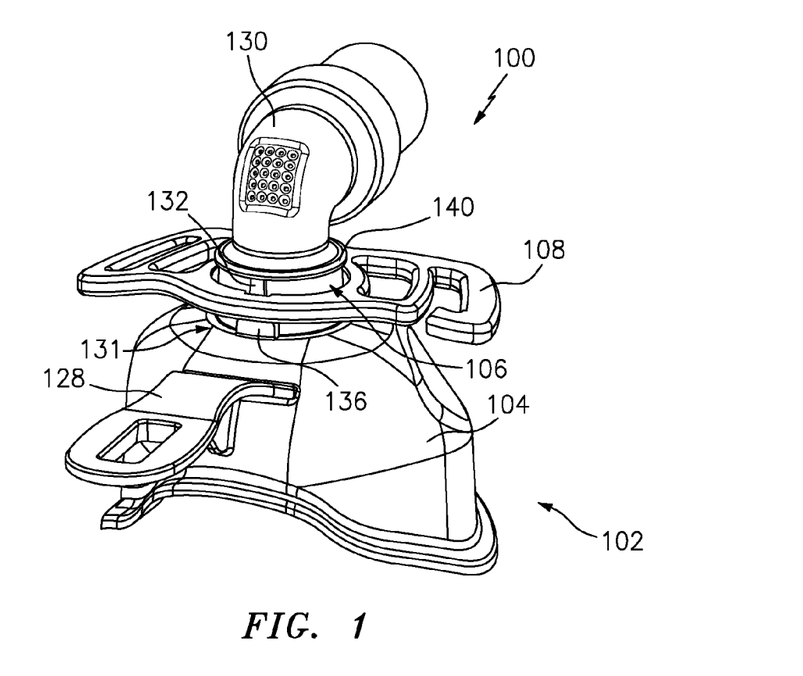
FIG. 1 is a perspective view of a CPAP mask having a preferred embodiment of Applicants' articulating headgear connector.
Figure 2:
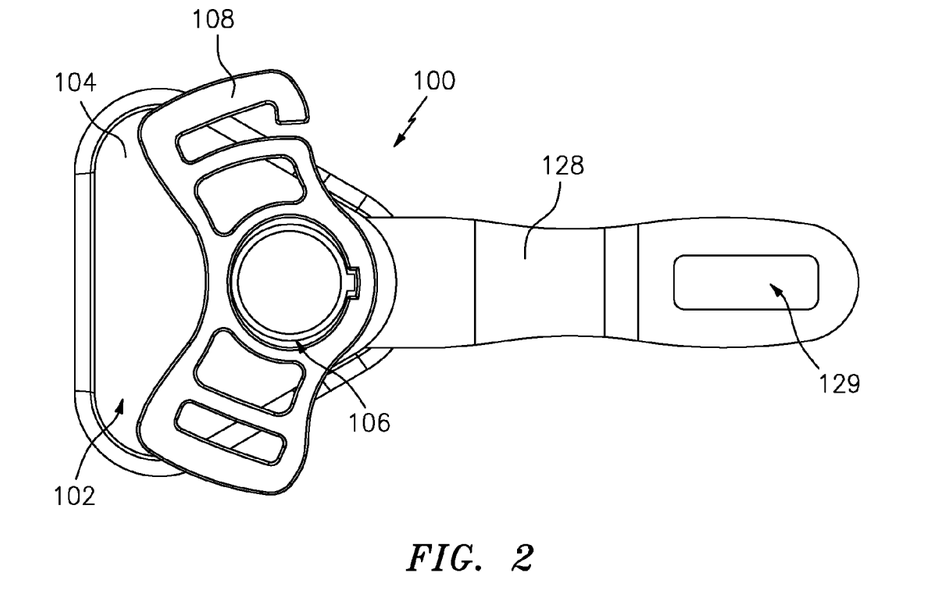
FIG. 2 is a front plan view of the mask, without an attached elbow piece shown in FIG. 1.
Figure 3A:
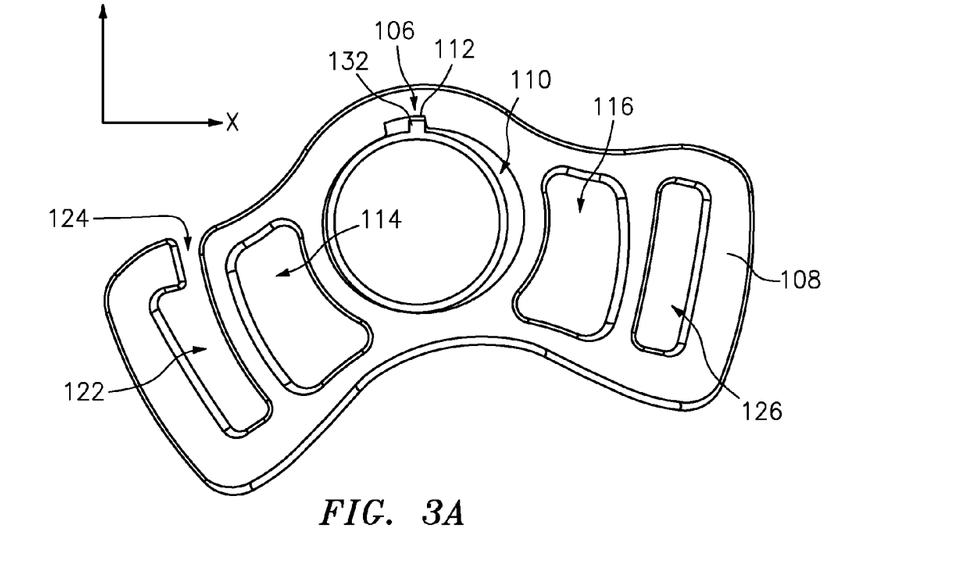
FIG. 3A is a frontal view of just the headgear connector rotated counterclockwise about the X-Y axes and stub tube.
Figure 3B:
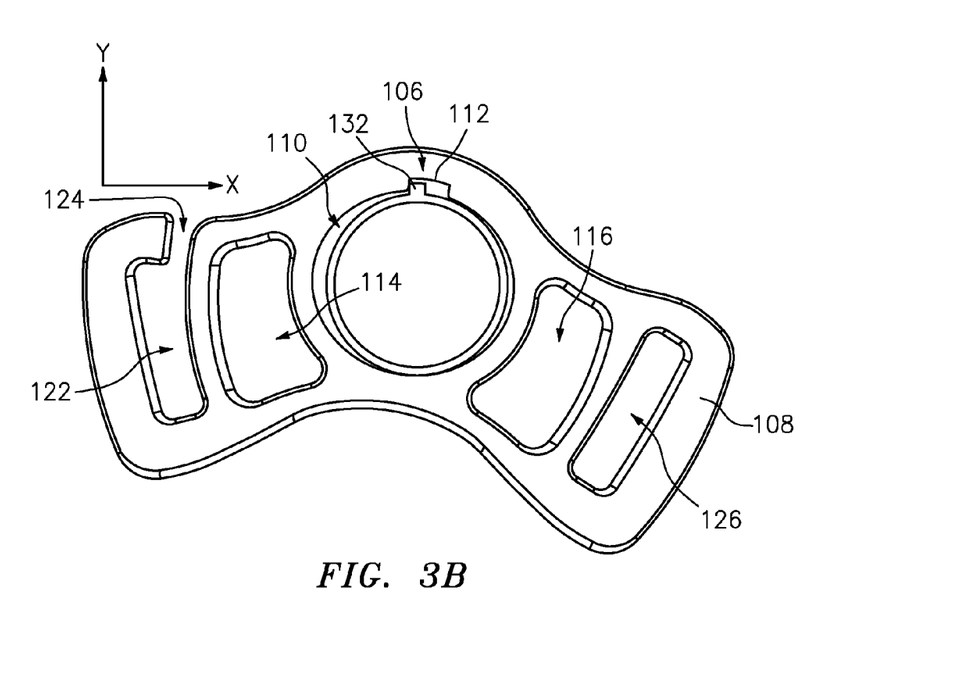
FIG. 3B is a frontal view of just the headgear connector rotated clockwise about the stub tube.

Referring to FIG. 1-6, Applicants' preferred embodiment 100 comprises: a respiratory mask (e.g., the illustrated CPAP mask) 102 having a plastic shell 104; the mask 102 has a stub tube (a.k.a. swivel post or elbow post) 106 extending outwardly from the shell 104; a headgear connector (a.k.a. retainer) 108 mounted loosely onto (a.k.a. supported on) the stub tube 106; and, wherein the headgear connector 108 can: slide forward on the stub tube 106 (i.e., move along the Z-axis); or rotate (a.k.a. rock) on the stub tube 106 along the X-Y axes (see FIGS. 3A, 3B).

FIGS. 2, 3A and 3B best show the preferred headgear connector 108. The headgear connector 108, made of plastic, is shaped like a bow. The headgear connector 108 includes a central hole 110 (see FIGS. 2, 3A, 3B) through which the stub tube 106 extends, with the connector loosely mounted (see FIGS. 2, 3A, 3B) onto the stub tube. There is a notch 112, preferably at top center of the stub tube 106, which opens up into the central hole 110. But for the notch 112, the hole 110 is oval.

Notch 112 locks the headgear connector 108 into a limited angle of rotation about the stub tube 106. The shape and size of the notch 112 can vary allowing the headgear connector 108 to have an increased or decreased range of motion. The weight of the headgear connector 108 was kept low by addition of extra holes 114, 116—one on both sides of hole 110.

The headgear connector 108 has two connection points for the headgear (not shown): a "Quick Release" slot 122, with an opening 124 at the top for quick removal of a headgear strap (not shown), on the left side of the stub tube 106; and a slot 126 to the right of the stub tube. Slot 126 is designed to hold another strap (not shown), but does not have an opening at its top. See FIGS. 3A, 3B.

The illustrated mask shell 104 also includes a plastic top arm 128 as a third point of contact for the headgear. Top arm 128 has a slot 129 for receiving two upper straps of the headgear (not shown). Top arm 128 is offset. That keeps the top arm and upper straps away from the wearer's forehead (not shown). That adds comfort and provides a more secure fit.

Figure 4:
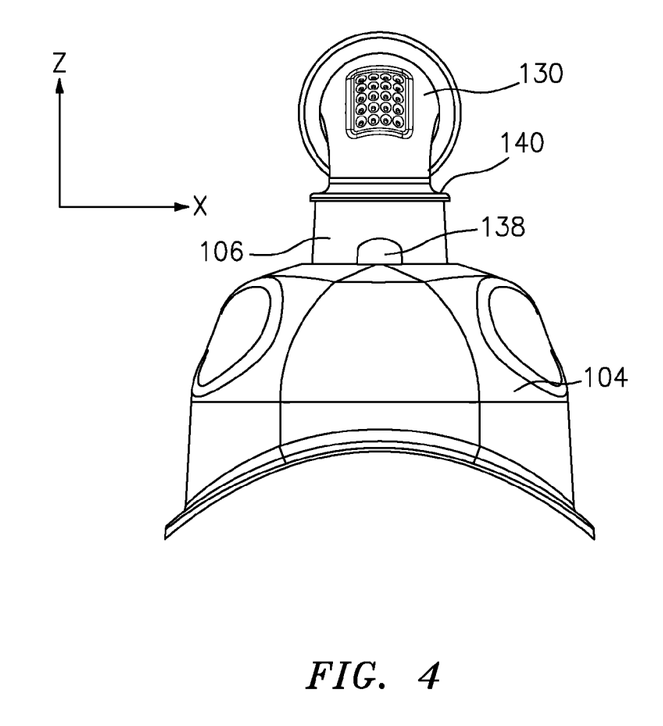
FIG. 4 is a bottom view of the FIG. 1 mask without the headgear connector, showing the stub tube, a bottom nib and the Z-axis.
Figure 5:
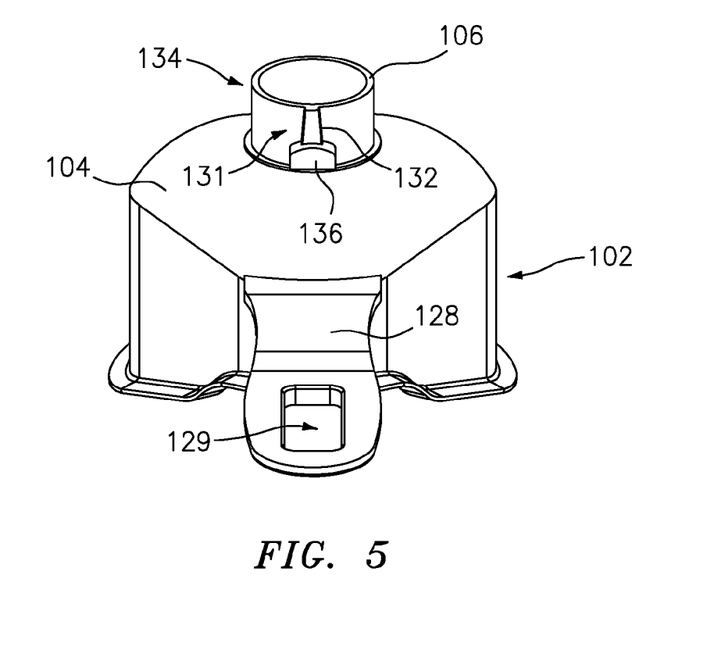
FIG. 5 is a perspective view of the mask without the headgear connector, showing a T-shaped nib along the top center of the stub tube.

Referring to FIGS. 1, 2 and 4, the mask shell 104 includes Applicants' stub tube 106, connected to the mask's inlet, located on the front center of the mask shell 104. A swiveling elbow piece 130 has an end pivotally attached within the tube. The elbow piece 130 has a series of exposed holes to carry out spent air. The elbow piece connects to a flexible plastic hose (not shown), which in turn is connected to a pressurized gas source (not shown). Applicants' stub tube 106 is modified on its outside, as compared to the prior art.

In the preferred embodiment, there is a generally T-shaped nib 131 (see FIGS. 1, 5 and 6) integral with and located along the top center of Applicants' stub tube 106. The T-shaped nib 131 comprises a "vertical" stem 132 of the "T" and a "horizontal" base 136.

The nib's stem 132 extends away from the mask shell 104, towards a free end 134 (see FIG. 5) of the stub tube 106. The stem, slightly narrower than notch 112, fits into the notch. Stem 132 acts as a guide rail for movement of the headgear connector 108 along the stem and the Z-axis (see FIG. 6); and the stem 132 limits the angle of rotation of the headgear connector 108 (see FIGS. 3A, 3B) about the X-Y axes.

The nib's horizontal base 136 is wider than the stem 132, as the T-shape's description indicates. Base 136 is integral with Applicant's stub tube 106 and is closer to the mask shell 104. Base 136 is wider than the notch. Therefore, the base 136 acts as a stop to limit backward movement of the connector 108, on the stub tube 106, along the Z-axis.

There is another stop 138 integral with and located at the bottom center of the Applicants' stub tube 106. Like the nib's horizontal base 136, stop 138 limits backward movement of the headgear connector 108, on the stub tube 106, along the Z-axis.

Forward movement on the stub tube, along the Z-axis, is limited by an annular lip 140 or ring of the elbow piece 130. The lip 140 acts as a forward stop.

But for the T-shaped nib 131 and bottom stop 138, the stub tube's outer contour is round in the preferred embodiment.

FIGS. 2, 3A, 3B illustrate the rocking motions of the headgear connector about the X-Y axes. FIG. 2 illustrates the headgear connector 108 in a neutral position. FIG. 3A illustrates the headgear connector 108 rotated counterclockwise (from its neutral position) about the X-Y axes. FIG. 3B illustrates the headgear connector 108 rotated clockwise from its neutral position. The stem 132 and notch 112 limit the degree of rotation about the X-Y axes to prevent disruption of the tubing (not shown) or headgear during therapy.

Figure 6:
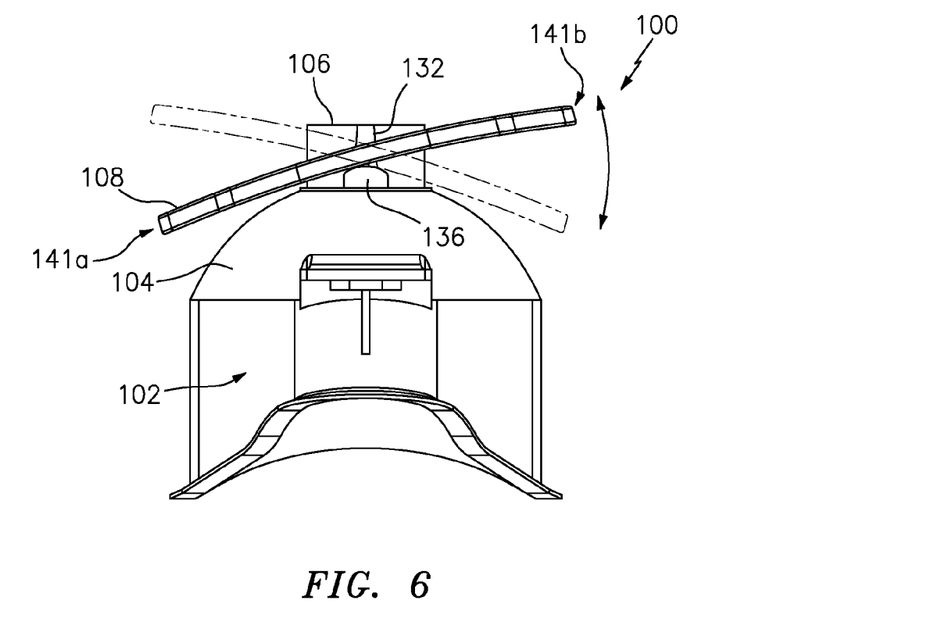
FIG. 6 is a top view of the mask showing the headgear connector pivoting against a base of the T-shaped nib.

Besides rotating or rocking about the X-Y axes, the tips or ends 141a, 141b of headgear connector 108 can seesaw back-and-forth on the Z-axis (see FIG. 6). For example, tip 141a can move closer to shell 104, with tip 141b moving farther away from shell 104; and vice versa. The base 136 of T-shaped nib 131 acts as a fulcrum. In the preferred embodiment, the bottom nib (a.k.a. stop) 138 also acts as a fulcrum for the seesaw motion of the connector 108.

Tossing and turning, by a mask wearer during sleep, creates forces on a worn mask (e.g., 102). As a force tugs the mask, Applicants' innovative headgear connector 108 rocks in the direction of the force relieving its effect.

The preferred embodiment can be thought of as including means for three-dimensional movement of the headgear connector 108 whereby the headgear connector can: slide forward on the stub tube 106; rock on the stub tube 106; and seesaw on the stub tube 106 with one end of the headgear connector 108 able to move closer to the mask shell 104, and later farther from the mask shell, than another end of the headgear connector. The means comprises the following elements and their interaction: the headgear connector 108 with its central hole 110, the stub tube 106, and the notch 112 riding on, or pivoting against, the nib 131.

Applicant's alternate embodiments, described below, depict other ways to achieve the three-dimensional movement means of the headgear connector.

Figure 7:
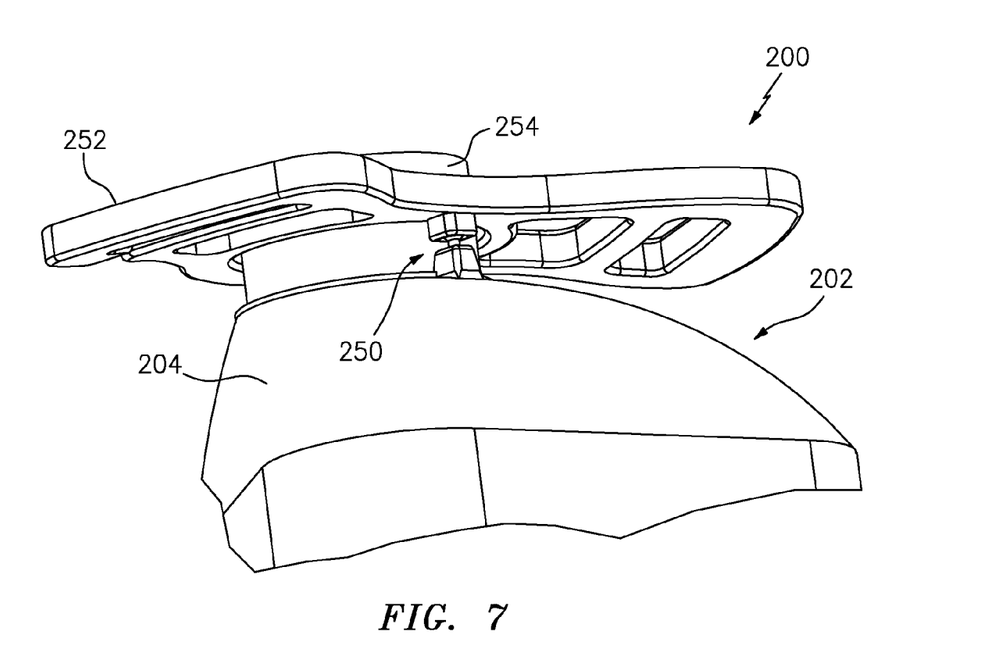
FIG. 7 depicts a second embodiment of Applicants' invention where a snap and ball connection are used to allow the headgear connector to articulate.

FIG. 7 depicts a second embodiment 200 of Applicants' "Headgear Connector for Respiratory Masks". Most of the components are the same as shown in Applicants' preferred embodiment 100. Identical elements in FIG. 7 are referenced by the same numbers, but with the prefix 200. For example, the mask shell 104 in FIGS. 1-6 is denoted by 204 in FIG. 7.

Applicants' second embodiment 200 uses a snap-and-ball connection 250 to allow the headgear connector 252 to articulate. The snap is a partially semi-spherical recess in the headgear connector 252, which receives the ball located on the mask 202. The recess has a depth larger than the ball's diameter. The ball fits securely into the snap and allows the headgear connector 252 to articulate about the X-Y-Z axes in response to mechanical forces. The illustration shows one snap-and-ball connection; however, there could be a snap and ball connection on both sides of the stub tube 254.

Headgear connector 252 is like headgear connector 108 but does not have a top notch in its center hole.

Stub tube 254 is like stub tube 106 but does not have the T-shaped nib 131 or stop 138.

Figure 8:
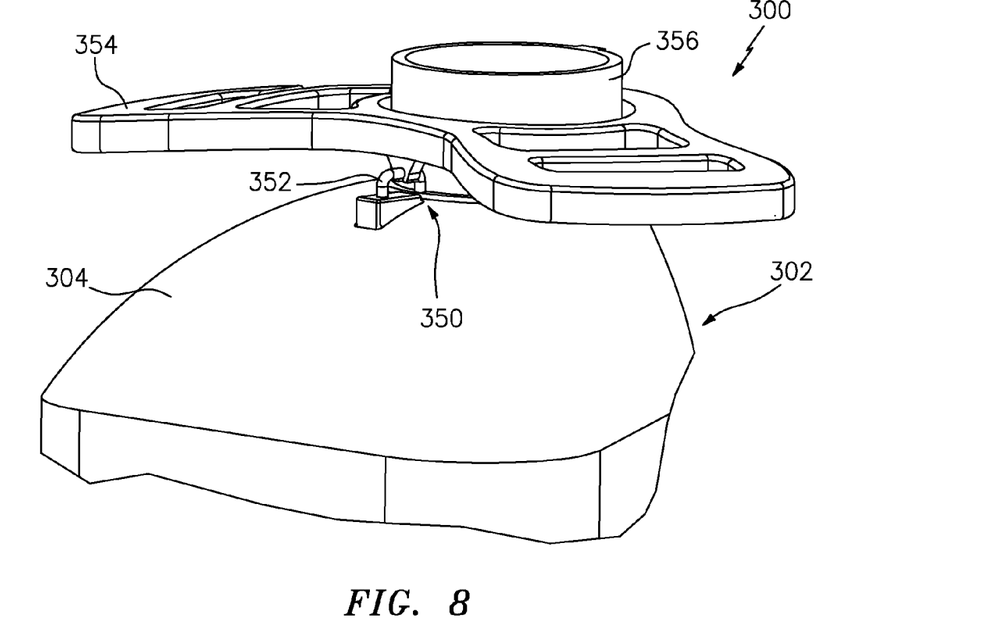
FIG. 8 depicts a third embodiment of Applicants' invention where a C-bracket and snap are used to allow the headgear connector to articulate.

FIG. 8 illustrates a third embodiment 300. Most of the components are the same as shown in Applicants' preferred embodiment 100. Identical elements in FIG. 8 are referenced by the same numbers, but with the prefix 300. For example, the mask shell 104 in FIGS. 1-6 is denoted by 304 in FIG. 8.

Applicants' third embodiment 300 uses a C-bracket 350 that snaps onto a bar 352 attached to shell 304. This configuration stabilizes the headgear connector 354 while allowing the connector to rock about the X-Y axes in response to mechanical forces. The illustration shows one C-bracket 350 and bar 352, however, there could be a similar set on both "sides" of the stub tube 356.

Headgear connector 354 is like headgear connector 108 but does not have a top notch in its center hole.

Stub tube 356 is like stub tube 106 but does not have the T-shaped nib 131 or stop 138.

Figure 9:
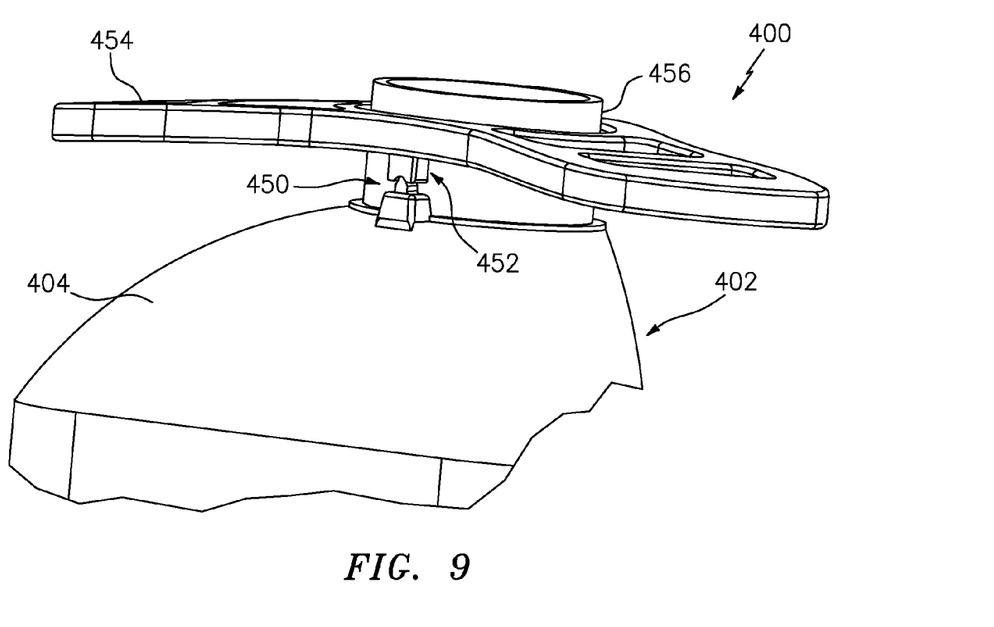
FIG. 9 depicts a fourth embodiment of Applicants' invention where a pyramid-and-groove connection is used to allow the headgear connector to articulate.

FIG. 9 illustrates a fourth embodiment 400. Most of the components are the same as shown in Applicants' preferred embodiment 100. Identical elements in FIG. 9 are referenced by the same numbers, but with the prefix 400. For example, the mask shell 104 in FIGS. 1-6 is denoted by 404 in FIG. 9.

Applicants' fourth embodiment uses: a pyramid 450 attached to the mask shell 404; and a groove 452 in the headgear connector 454 which receives the pyramid. The pyramid 450 and groove 452 stabilize the headgear connector 454 while allowing it to move about the X-Y axes in response to mechanical forces. The illustration shows one pyramid 450 and groove 452 mechanism, however, there could be a pyramid-and-groove connection on both "sides" of the stub tube 456.

Headgear connector 454 is like headgear connector 108 but does not have a top notch in its center hole.

Stub tube 456 is like stub tube 106 but does not have the T-shaped nib 131 or stop 138.

Though not shown, the mask shell in each embodiment can include recesses (e.g., adjacent slots 122, 126) to prevent the headgear straps from restraining movement of the headgear connector.

Embodiments of the present invention provide masks that perform better ergonomically and provide increased comfort to a sleeping or recumbent user. The nib features on the stub tube, when combined with the unique design of the headgear connector, create an articulating mechanism that provides comfort and resilience during movement, allowing for a reliable seal.

It should be understood that obvious structural modifications can be made without departing from the spirit or scope of the invention. For example, while FIGS. 1-9 disclose a nasal mask, the invention could be used with other masks, such as a full mask or an oronasal mask. In addition, instead of the headgear connector's central hole being oval and the stub tube's outer contour being round, they both could be round or oval.

We claim:

1. A device comprising:
   a. a respiratory mask having a mask shell;
   b. the mask has a stub tube extending outwardly from the shell;
   c. a headgear connector supported on the stub tube; and
   d. means for three-dimensional movement of the headgear connector, relative to the stub tube, whereby the headgear connector can:
      i. slide on the stub tube, along a Z-axis, away from the mask shell and later towards the shell;
      ii. rotate clockwise and counterclockwise about the stub tube in a plane defined by X- and Y-axes; and
      iii. seesaw on the stub tube with one end of the headgear connector able to move closer to the mask shell while an opposite end of the headgear connector moves farther away from the shell, and later the opposite end can move closest to the mask shell while the one end moves farther away from the shell;
   e. wherein the means comprises:
      i. the headgear connector has a central hole through which the stub tube extends;
      ii. the headgear connector has a notch which opens into the central hole;
      iii. the notch straddles a T-shaped nib, narrower than the notch, located on an outer surface of the stub tube; and
      iv. the T-shaped nib comprises a stem, extending toward a free end of the stub tube, and a perpendicular base adjacent the shell.

2. The device of claim 1 wherein the mask is a CPAP mask.

* * * * *